(12) United States Patent  (10) Patent No.: US 9,393,412 B2
Strahl et al.  (45) Date of Patent: Jul. 19, 2016

(54) MULTI-CHANNEL OBJECT-ORIENTED AUDIO BITSTREAM PROCESSOR FOR COCHLEAR IMPLANTS

(71) Applicant: MED-EL Elektromedizinische Geraete GmbH, Innsbruck (AT)

(72) Inventors: Stefan Strahl, Innsbruck (AT); Cornelia Falch, Rum (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 14/136,129

(22) Filed: Dec. 20, 2013

(65) Prior Publication Data

US 2014/0128940 A1 May 8, 2014

Related U.S. Application Data

(63) Continuation-in-part of application No. 12/817,363, filed on Jun. 17, 2010, now abandoned.

(60) Provisional application No. 61/187,742, filed on Jun. 17, 2009.

(51) Int. Cl.
*A61N 1/36* (2006.01)
*H04R 25/00* (2006.01)

(52) U.S. Cl.
CPC .......... *A61N 1/36032* (2013.01); *H04R 25/505* (2013.01); *H04S 2420/03* (2013.01)

(58) Field of Classification Search
CPC ................................. A61N 1/36032
USPC ............................................. 607/57

See application file for complete search history.

(56) References Cited

U.S. PATENT DOCUMENTS

| 4,051,331 | A | 9/1977 | Strong et al. |
| 5,434,924 | A | 7/1995 | Jampolsky |
| 5,825,894 | A | 10/1998 | Shennib |
| 6,868,163 | B1 | 3/2005 | Goldstein |
| 6,910,013 | B2 * | 6/2005 | Allegro et al. ............... 704/256 |

(Continued)

FOREIGN PATENT DOCUMENTS

| WO | WO 00/01200 | 1/2000 |
| WO | WO 01/19135 | 3/2001 |
| WO | WO 2006/119069 | 11/2006 |

OTHER PUBLICATIONS

Engdegard, et al, "Spatial Audio Object coding (SAOC)—the Upcoming MPEG Standard on parametric Object Based Audio Coding", AES Convention 124; May 2008, AES, 60 East $42^{nd}$ Street, Room 2520, NY, NY 10165-2520; May 1, 2008 XP040508593.

(Continued)

*Primary Examiner* — Alyssa M Alter
(74) *Attorney, Agent, or Firm* — Sunstein Kann Murphy & Timbers LLP

(57) ABSTRACT

An audio-cochlear implant processor device for a hearing impaired listener is described. An input signal decoder decodes an audio input data signal into a corresponding multi-channel audio signal representing multiple audio objects. An audio processor adjusts the multi-channel audio output based on user-specific hearing impairment characteristics to produce a processed audio output to a cochlear implant audio processor with auditory scene analysis (ASA) cues for the hearing impaired listener.

17 Claims, 2 Drawing Sheets

(56) References Cited

U.S. PATENT DOCUMENTS

| | | |
|---|---|---|
| 7,072,717 B1 | 7/2006 | Wolf et al. |
| 7,149,583 B1 | 12/2006 | Litvak |
| 7,209,789 B2 | 4/2007 | Zierhofer |
| 7,225,027 B2 | 5/2007 | Zeng et al. |
| 7,251,530 B1 | 7/2007 | Overstreet et al. |
| 7,310,558 B2 | 12/2007 | Van Hoesel |
| 7,421,298 B2 | 9/2008 | Daly et al. |
| 7,986,789 B2 | 7/2011 | Purnhagen et al. |
| 2005/0107843 A1 | 5/2005 | McDermott et al. |
| 2005/0135644 A1 | 6/2005 | Qi |
| 2005/0203589 A1 | 9/2005 | Zierhofer |
| 2006/0052841 A1 | 3/2006 | Daly et al. |
| 2006/0100672 A1 | 5/2006 | Litvak |
| 2006/0265061 A1 | 11/2006 | Kwon et al. |
| 2007/0183609 A1 | 8/2007 | Jenn |
| 2007/0258607 A1 | 11/2007 | Purnhagen et al. |
| 2007/0282393 A1 | 12/2007 | Marquis |
| 2008/0101635 A1* | 5/2008 | Dijkstra ............... H04R 25/30 381/315 |
| 2008/0172108 A1 | 7/2008 | Zierhofer et al. |
| 2009/0067634 A1 | 3/2009 | Oh et al. |
| 2010/0014692 A1* | 1/2010 | Schreiner ............. H04S 3/008 381/119 |
| 2010/0086136 A1 | 4/2010 | Beckmann et al. |
| 2010/0098274 A1 | 4/2010 | Hannemann et al. |
| 2010/0135511 A1 | 6/2010 | Pontoppidan |
| 2010/0198300 A1 | 8/2010 | Smith |
| 2010/0226499 A1 | 9/2010 | De Bruijn et al. |
| 2010/0246867 A1 | 9/2010 | Lenhardt et al. |
| 2010/0322446 A1 | 12/2010 | Strahl |
| 2011/0075848 A1 | 3/2011 | Purnhagen et al. |
| 2012/0051569 A1 | 3/2012 | Blamey et al. |

OTHER PUBLICATIONS

ITU Study Group, "Call for Proposals on Spatial Audio Object Coding", *ISO/IEC MPEG & ITU-T BCEG 9ISO/IEC JTC1/SC29/WG11 and ITU-T SG16*, No. N8853, Feb. 19, 2007, XP030015347.

Jung, Yang-Won, et al, "Personalized Music Service Based on Parametric Object Oriented Spatial Audio Coding", *AES 34th International Conference: New Trends in Audio for Mobile and Handheld Devices*; Aug. 1, 2008, AES, 60 East 42nd Street, Room 2520, NY, NY 10165-2520; XP040508529.

European Patent Office, International Search Report and Written Opinion, PCT/US2010/038948; Sep. 7, 2010.

\* cited by examiner

MULTI-CHANNEL OBJECT-ORIENTED AUDIO BITSTREAM PROCESSOR FOR COCHLEAR IMPLANTS This application claims priority from U.S. patent application Ser. No. 12/817,363, filed Jun. 17, 2010, which in turn claims priority from U.S. Provisional Patent Application 61/187,742, filed Jun. 17, 2009; which are incorporated herein by reference.

FIELD OF THE INVENTION

The present invention relates to medical devices, and more specifically to audio signal processing in hearing prosthetic devices.

BACKGROUND ART

The human auditory processing system segregates sound objects from complex auditory scenes using several binaural cues such as interaural time and level differences (ITD/ILD) and monaural cues such as harmonicity or common onset. This process is known as auditory scene analysis (ASA) as described more fully in A. S. Bregman *Auditory Scene Analysis: The Perceptual Organization of Sound*, MIT Press, Cambridge, Mass. (1990), incorporated herein by reference.

Hearing impaired patients have difficulties successfully performing such an auditory scene analysis even with a hearing prosthesis such as a conventional hearing aid, a middle-ear prosthesis, a bone-anchored hearing prosthesis, a cochlear implant (CI), or an auditory brainstem implant (ABI). Cues such as harmonicity, which the normal human auditory processing system uses for ASA, are not correctly reproduced by the current cochlear implants and auditory brainstem implants. This is especially a problem for audio recordings and live audio streaming. Processing methods such as directional microphones or steerable beamforming do not help hearing prostheses handle audio recordings played with standard sound systems, (i.e. stereo loudspeakers or headphones) because such techniques require true spatial sound sources.

Because of such problems, hearing aid users often are unable to listen to a single individual sound source within a mixture of multiple sound sources. In the case of understanding speech, this translates into reduced speech intelligibility. In the case of music, musical perception is degraded due to the inability to successfully isolate and follow individual instruments.

To assist cochlear implant users in performing an auditory scene analysis, an alteration of the sound signals is normally applied that emphasizes the sound sources of interest; see e.g., U.S. Pat. No. 8,369,958, which is incorporated herein by reference.

SUMMARY OF THE INVENTION

Embodiments of the present invention are directed to an audio-cochlear implant processor device and corresponding method for a hearing impaired listener. An input signal decoder decodes an audio input data signal into a corresponding multi-channel audio signal representing multiple (monophonic or stereophonic) audio objects. An audio processor adjusts the multi-channel audio output based on user-specific hearing impairment characteristics to produce a processed audio output to a cochlear implant audio processor that provides auditory scene analysis (ASA) cues for the hearing impaired listener.

Each channel of the multi-channel audio signal may represent a mix of a plurality of audio objects, and the multi-channel audio signal may include partial or complete source separation demixing information for the audio objects in each channel. The audio input data signal may be based on an audio recording playback signal or a real time audio source. The user-specific hearing impairment characteristics may include user audiogram data and/or user-specific processing fit data and/or a parameter control information feedback signal from the cochlear implant audio processor. Adjusting the multi-channel audio output may further be based on a coding strategy associated with the post-processed audio output. The device may more specifically be part of a conventional hearing aid system, a middle ear prosthesis system or a cochlear implant system.

DETAILED DESCRIPTION OF SPECIFIC EMBODIMENTS

Some of the aforementioned problems can be avoided by using properly prepared audio recordings and live audio streaming with a mix (or scene) of individual tracks of the audio objects that are present. The individual audio object bitstreams can be initially processed before delivering them to a device-specific processor such as a cochlear implant processor or an auditory brainstem implant processor. The information about the mixing process can be supplied to the audio processor via a parameter interface. But when no such information is available, the audio processor can blindly estimate these parameters, which could be realized using techniques such as informed, guided and semi-blind source separation, described for example in A. Cichocki, S. Amari *Adaptive Blind Signal and Image Processing*, Wiley (2002), which is incorporated herein by reference. Another approach for delivering a multi-channel single object audio format is presented in the MPEG standard "Spatial Audio Object Coding" (SAOC) that allows access to all the separately recorded sound sources at recording time.

To date, no approach has been published that jointly exploits listener-specific hearing impairment characteristics (e.g. audiogram or modulation-detection threshold), audio processor settings (e.g. coding strategy, fitting map, . . . ), and single audio object-specific information to optimize the playback of audio recordings or live-streaming by processing and remixing the sound sources for the individual hearing impaired listener. Nor has any existing approach described the direct mapping of relevant audio object meta data (i.e. parameters of an MPEG-SAOC bitstream) to a cochlear implant audio processor.

Embodiments of the present invention are directed to an audio processor device and corresponding method that optimizes the playback of audio recordings and/or live-streaming by processing and remixing the sound sources for the individual hearing impaired listener to reflect listener-specific hearing impairment characteristics, audio processor settings and single audio object-specific information. Unlike the arrangement described in U.S. Pat. No. 8,369,958 which processes the individual speech signals individually, embodiments of the present invention support combined signal processing of the audio signals as well.

Figure 1:
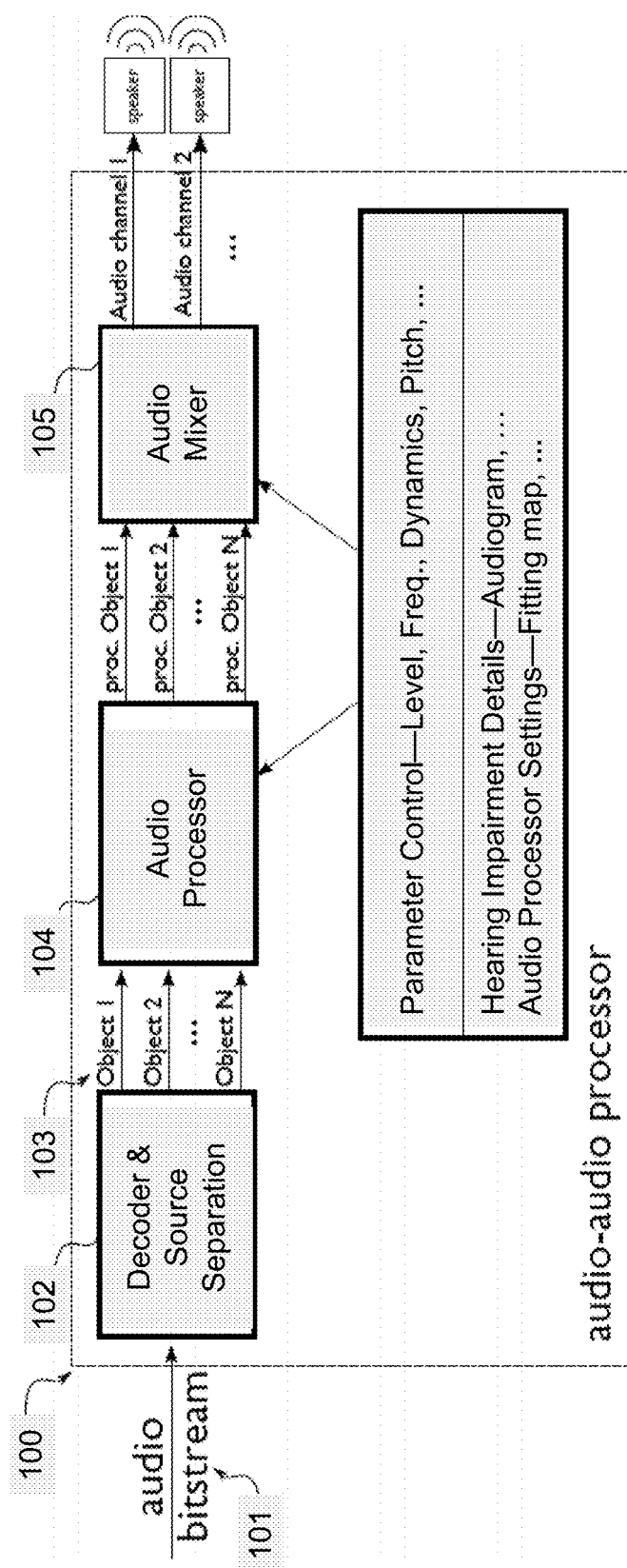
FIG. 1 shows an example of an audio processor device according to one specific embodiment of the present invention.

FIG. 1 shows an example of an audio-to-audio processor device 100 having an input signal decoder 102 that uses a source separation algorithm to decode an audio bitstream input 101 data signal into a corresponding multi-channel audio signal representing multiple (monophonic or stereophonic) audio objects 103. An audio processor 104 then adjusts the multi-channel audio output based on user-specific hearing impairment characteristics, and an audio mixer 105 combines the processed audio output into audio output channels such as a standard stereo audio signal or a direct audio input for speakers or of a hearing aid or CI, e.g. via direct audio link or via telecoil. Either or both of the audio processor 104 and the audio mixer 105 take into account (manually or automatically) the details of the users specific hearing impairment (e.g. audiogram, etc.) and an audio processor setting (e.g. selected coding strategy in the subsequent CI processor, fitting map, patient specific impedance values of stimulation electrodes, patient specific available dynamic range of the stimulation electrodes, . . . ) to produce a processed audio output providing auditory scene analysis (ASA) cues for the hearing impaired listener.

More specifically, the audio processor 104 can adjust the multi-channel audio output based on the computation of the contribution of each audio object 103 to the stimulation pattern of the cochlear implant. For each audio object 103, the audio processor 104 can compute the masking and distortion effects using known hearing impairment details such as audiogram or modulation detection threshold. Then using an optimization algorithm, the audio processor 104 can exploit these masking and distortion effects to yield an improved hearing sensation of the impaired listener. Specifically, the contribution of one audio object 103 being masked by another one may be identified by the audio processor 104 and neglected in the subsequent audio mixer 105. Distortion from combining the audio objects 103 into an audio channel may be estimated and suppressed (or entirely cancelled) by the audio processor 104 to minimize their degrading effects on the audio output of audio mixer 105 that will be perceived by the hearing impaired person.

A conventional audio signal includes some kinds of information that a CI user may not be able to resolve due to his/her individual hearing impairment. On the other hand, the CI processor is confronted with the entire audio signal even though it only needs to process a minor part of it. This may lead to a non-optimal processing and coding since the discrimination between signal content the CI user can and cannot exploit ("hear") represents a significant challenge to the CI processor. Examples of irrelevant signal content are (i) parts of the audio signal lying in a frequency region the CI user cannot perceive, (ii) separate audio objects the CI user cannot identify as such because of the reduced frequency resolution, (iii) echoic sections of a signal, etc. The audio-to-audio processor 100 may cooperate with the CI processor by working as a pre-filter suppressing or fully cancelling signal content and/or audio object(s), based on user-specific data, beyond the CI user's hearing threshold. This "reduced" or sparse audio signal ensures more selective and target-oriented CI processing and coding.

An example of one specific pseudo code algorithm that may be used by the audio processor 104 is as follows:

```
# compute mutual distortion of current audio objects
distortion = compute_distortions(audio_objects o)
```

```
# minimize mutual distortions of audio objects
do
    # minimize distortion by transforming audio_objects
    for all audio_objects o
        o = minimize_distortion(o,distortion,user_CI_fitting,
user_hearing_impairment_details)
    end
    distortion_old = distortion
    distortion = compute_distortions(audio_objects o)
    distortion_improvement = distortion_old - distortion
while distortion_improvement > 0
function compute_distortions(audio_objects o)
    for all audio_objects o
        for all electrodes e
            stimpattern(o,e) =
calc_contribution(audio_object(o),e,user_CI_fitting);
        end
    end
    # compute spread of excitation due to electric field
    for all audio_objects o
        channelinteraction(o) =
calc_channelinteraction(stimpattern(o,:));
    end
    # compute distortion of single object due to other objects
    for all audio_objects o_target
        for all other audio_objects o_masker
            distortion(o_target,o_masker) =
calc_masking(stimpattern(o_target),channelinteraction(o_masker),
user_hearing_impairment_details)
        end
    end
    return distortion
```

Figure 2:
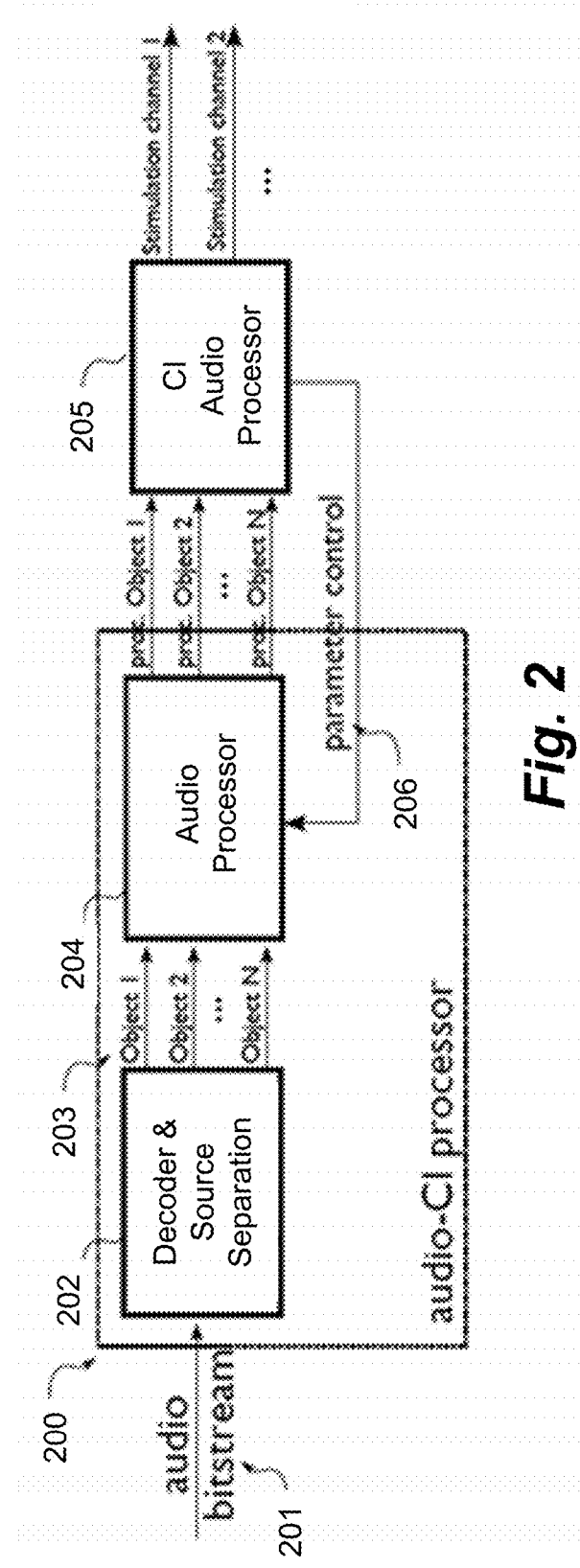
FIG. 2 shows an example of another specific embodiment of an audio processor device using the present invention.

FIG. 2 shows an example of another arrangement of an audio-to-CI processor device 200 having an input signal decoder 202 for the audio bitstream input 201, an audio processor 204 and an extended cochlear implant sound processor 205. In contrast to the arrangement described with regards to FIG. 1, in this system, the processed audio objects 203 in the processed audio output (from the audio processor 204) are made directly available to the cochlear implant CI sound processor 205, for example, by using a cable or a wireless communication link. This additional information related to the number of the sound sources present in the audio input data signal and their waveforms allows the cochlear implant sound processor 205 to optimize its signal processing to improve the auditory scene analysis (ASA) by the hearing impaired listener as compared to a standard audio processor. This additional audio object information also allows new signal processing algorithms to be used based on the separated sound objects. That is, based on the known user-specific hearing impairment characteristics and the chosen signal processing parameters, the audio-to-CI processor device 200 can control the input signal decoder 202, audio processor 204 and extended cochlear implant sound processor 205 to further improve the listening performance of the hearing impaired user. Real-time parameter control information 206 on the current stimulus parameters and personal fitting data provided by the CI sound processor 205 can be fed back to the audio processor 204 to allow for a real-time update of the estimated distortions and needed processing of the audio objects 203.

One apparent difference between the arrangements of FIGS. 1 and 2 is that in FIG. 2, the CI sound processor 205 receives all processed sound objects separately without being mixed and the CI sound processor 205 performs the mixing function, not in an identical way as in the audio mixer 105 in FIG. 1, but inherently within the selected coding strategy of the CI sound processor 205. Nevertheless, the examples given in the following discussion as to FIG. 1 may also apply to the arrangement in FIG. 2 considering that the function of Audio Mixer 105 may be performed by CI sound processor 205. One other difference between the arrangement of FIGS. 1 and 2 is a back channel 206 in the arrangement of FIG. 2 which allows for automatic and continuous adjustment of parameter settings of the audio processor 204.

An illustrative scenario in which such arrangements would be useful is a case of a movie scene with two voice tracks of a male actor and a female actor talking in front of a third sound object such as an operating television set. The information of the user-specific hearing impairment characteristics and the settings of the hearing prosthesis settings of the CI sound processor 204 may be used in the audio processor 104/204 to determine that the female voice has a fundamental frequency highly overlapping with the frequency spectrum of the speech-like noise from the television and that both audio objects, female voice and TV background babble noise are active simultaneously. Furthermore, the same information may be used to determine that this (partly or fully) overlapping in frequency space and time of the audio objects 103/203 will lead to adverse masking effects, i.e. one audio object renders one or more other audio objects (partly or fully) imperceptible. For the described scenario such masking may e.g. yield reduced speech intelligibility of the actress for the hearing impaired listener. For each individual audio object, the audio processor device 100/200 can change the corresponding audio properties such as level, frequency dynamics, and/or pitch, so that for example an appropriate increase in level of the female speaker and a corresponding decrease in level of the TV could be applied in the audio mixer 105 or the CI sound processor 205 to increase the speech intelligibility of the female speaker. Another similar example would be pitch shifts of the sound objects within the audio processor 104/204 to minimize frequency overlapping signal parts so that for a user of a cochlear implant or auditory brainstem implant the two objects are mapped to two different electrodes.

Another example in which embodiments of the invention could be useful represents any music played by a few (e.g. pop band, ensemble) or many (e.g. orchestra, choir) musicians (e.g. instrumentalists and/or singers). A user of the audio processor device 100/200 could listen to the same music, e.g. a piece of orchestra recording, multiple times, once with emphasis on e.g. the strings, a second time with emphasis on the woodwinds, etc. This is enabled because the audio mixer 105 or the CI sound processor 204 adds all N separate sound sources into the M output channels of the listener's sound system (e.g., M=2 for a stereo sound system). For every sound source, individual level (and/or other audio object- and user-specific) parameters can be applied depending on the hearing impaired listener's predicted intelligibility and/or personal settings. This would allow a user to repeatedly listen to complex auditory scenes with changing audio emphasis on different audio objects 103/203. For example, two instruments with similar spectra might fall in the same analysis filters of the CI sound processor 204 and could thereby be perceived (e.g., based on an artificially introduced harmonicity cue) as a single object with mismatching time-onsets. This disturbance could be minimized or even cancelled by lowering the level of one instrument within the audio mixer 105 or the CI sound processor 204, or, if possible, by changing the object's pitch within the audio processor 104/204, i.e. shifting it to other (non-conflicting) frequency regions of the analysis filter, thereby providing enhanced listening comfort to the hearing impaired user.

Another illustrative scenario could be a broadcast of a discussion with many competing speakers, who naturally tend to talk at the same time quite frequently. Hearing impaired listeners especially suffer from those double talk situations, severely degrading their listening comfort. The audio processor device 100/200 may improve the challenging listening situation by utilizing the additionally available object (i.e. speaker) related information. For example, depending on a priority list that may be either automatically computed or user controlled, an intelligibility measure or priority index may be computed for every audio object 103 in the mixed presentation. Audio objects 103 having a relatively low priority that degrade the intelligibility of other audio objects 103 with a higher priority, may thus be suppressed or entirely removed from the audio mixture within the audio 105 or CI sound processor 204 for better ASA.

Another illustrative scenario would be if a CI user has an electrode contact with an usually high impedance that results in a reduced dynamic range compared to the other electrode contacts. The audio processor device 100/200 could use this information determined from the settings of the CI sound processor 205 to balance the compression of all auditory objects 103 to compensate the unequal dynamic range between the electrodes.

Another illustrative scenario would be that the audio-to-CI processor device 200 might be presenting a radio show having changing speech and music content. During a switch from music to speech the CI sound processor 205 could signal via the parameter control connection 206 an (automatic) change of its scene classifier from using optimized settings for speech to optimized settings for music. This information can be used in the audio processor 204 to also prioritize auditory objects having speech content.

Another illustrative scenario would be that the audio-to-CI processor device 200 might be presenting music to the CI sound processor 205 in a mixed mode configuration where the microphones of the CI sound processor 205 are active and their signals are mixed into the music coming from the audio-to-CI processor device 200. If the CI user is in a windy environment the wind noise cancellation functionality of the CI sound processor 205 will be activated and dampen the low frequencies. The (automatic) activation of the wind noise cancellation processing in the CI sound processor 205 can be detected via the parameter control connection 206 and compensated within the audio processor 204 by enhancing the low frequencies of the processed objects (output of 204).

Embodiments of the invention may be implemented in whole or in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in whole or in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention. For example, while the foregoing description uses a cochlear implant as an example, it should be apparent that an auditory brainstem implant or a multichannel hearing aid may be used instead.

What is claimed is:

1. An audio-cochlear implant processor device for a hearing impaired listener, the device comprising:
   an input signal decoder configured for decoding an audio input data signal into a corresponding multi-channel audio signal representing a plurality of audio objects; and
   an audio processor configured for adjusting the multi-channel audio signal based on a computation of masking and distortion using known user-specific hearing impairment characteristics to suppress degrading effects of the masking and distortion and produce a processed audio output to a cochlear implant audio processor providing auditory scene analysis (ASA) cues for the hearing impaired listener.

2. A device according to claim 1, wherein the input signal decoder is configured to represent a mix of a plurality of audio objects in each channel of the multi-channel audio signal.

3. A device according to claim 2, wherein the input signal decoder is configured to include source separation demixing information for the audio objects in each channel of the multi-channel audio signal.

4. A device according to claim 1, wherein the input signal decoder is configured for decoding an audio input data signal that is based on an audio recording playback signal.

5. A device according to claim 1, wherein the input signal decoder is configured for decoding an audio input data signal that is based on real time audio sources.

6. A device according to claim 1, wherein the audio processor is configured for adjusting the multi-channel audio signal based on user-specific hearing impairment characteristics that include user audiogram data.

7. A device according to claim 1, wherein the audio processor is configured for adjusting the multi-channel audio signal based on user-specific hearing impairment characteristics that include user-specific processing fit data.

8. A device according to claim 1, wherein the audio processor is configured for adjusting the multi-channel audio signal based on user-specific hearing impairment characteristics that include a parameter control information feedback signal from the cochlear implant audio processor.

9. A computer-implemented method employing at least one hardware implemented computer processor for processing audio signals for a cochlear implant processor of a hearing impaired listener, the method comprising:
   automatically decoding an audio input data signal into a corresponding multi-channel audio signal representing a plurality of audio objects; and
   adjusting the multi-channel audio signal based on a computation of masking and distortion using known user-specific hearing impairment characteristics to suppress degrading effects of the masking and distortion and produce a processed audio output to the cochlear implant audio processor providing auditory scene analysis (ASA) cues for the hearing impaired listener.

10. A method according to claim 9, wherein each channel of the multi-channel audio signal represents a mix of a plurality of audio objects.

11. A method according to claim 10, wherein the multi-channel audio signal includes source separation demixing information for the audio objects in each channel.

12. A method according to claim 9, wherein the audio input data signal is based on an audio recording playback signal.

13. A method according to claim 9, wherein the audio input data signal is based on real time audio sources.

14. A method according to claim 9, wherein the user-specific hearing impairment characteristics include user audiogram data.

15. A method according to claim 9, wherein the user-specific hearing impairment characteristics include user-specific processing fit data.

16. A method according to claim 9, wherein the user-specific hearing impairment characteristics include a parameter control information feedback signal from the cochlear implant audio processor.

17. A cochlear implant system using the method according to any of claims 9-16.

* * * * *